United States Patent [19]

Fox et al.

[11] Patent Number: 5,395,361
[45] Date of Patent: Mar. 7, 1995

[54] EXPANDABLE FIBEROPTIC CATHETER AND METHOD OF INTRALUMINAL LASER TRANSMISSION

[75] Inventors: Kenneth R. Fox, Arlington; A. Arthur Coster, Alex, both of Va.

[73] Assignee: Pillco Limited Partnership, Arlington, Va.

[21] Appl. No.: 260,818

[22] Filed: Jun. 16, 1994

[51] Int. Cl.⁶ .............................................. A61B 17/36
[52] U.S. Cl. .......................................... 606/15; 606/7; 606/16
[58] Field of Search ............................ 606/7, 2, 10–17, 606/193, 194; 604/19, 21; 128/6

[56] References Cited

U.S. PATENT DOCUMENTS 4,790,310  12/1988  Ginsburg et al. ....................... 606/7
5,176,674   1/1993  Hofmann ................................ 606/7
5,203,777   4/1993  Müller et al. .......................... 606/7
5,226,430   7/1993  Spears et al. ...................... 606/7 X Primary Examiner—Peter A. Aschenbrenner
Attorney, Agent, or Firm—Wigman, Cohen, Leitner & Myers

[57] ABSTRACT

A catheter system for intraluminal laser surgery is disclosed. The catheter system comprises an elastically expansible catheter sheath housing a plurality of optical fibers arranged in a circular array about an inflatable balloon. Inflation and deflation of the balloon expands and contracts the diameters of both the optical fiber array and the catheter. Throughout inflation and deflation of the balloon the distal ends of the fiberoptic light guides are maintained generally parallel to the lumen wall thereby maximizing the safety and efficacy of the procedure.

20 Claims, 2 Drawing Sheets

EXPANDABLE FIBEROPTIC CATHETER AND METHOD OF INTRALUMINAL LASER TRANSMISSION

BACKGROUND OF THE INVENTION

The present invention relates to an expandable fiberoptic catheter and a method of transmitting laser energy through a catheter, especially for intraluminal surgical procedures such as laser angioplasty, laser atherectomy, laser thrombolysis, laser lithotripsy and the like.

It is well known that laser energy may be transmitted through a plurality of optical fibers housed in a relatively flexible tubular catheter which may be inserted into a body lumen, such as a blood vessel, ureter, fallopian tube, cerebral artery, etc., to remove obstructions in the lumen. Our prior U.S. Pat. Nos. 4,784,132; 4,800,876; 4,848,336 and 5,041,108, the disclosures of which are incorporated herein by reference, describe apparatus, including catheters, and methods that may be used for the intraluminal transmission of laser energy through a plurality of optical fibers to remove obstructions in a body lumen. U.S. Pat. No. 5,250,045 discloses another type of catheter that may also be used for the intraluminal transmission of laser energy. Such catheters as are in use at the present time for laser angioplasty and similar procedures typically have a central passage or tube which receives a guide wire inserted into the body lumen prior to introduction of the catheter.

Typical of commercially available laser angioplasty equipment are the CVX-300 Excimer Laser Angioplasty System and Extreme and Vitesse catheters manufactured by The Spectranetics Corporation of Colorado Springs, Colo. and the DYMER 200+ Excimer Laser Angioplasty System and LITVACK catheters manufactured by Advanced Interventional Systems, Inc. of Irvine, Calif.

One common drawback of most catheters which house a plurality of optical fibers, especially those for use in removing obstruction from small diameter body lumens, such as blood vessels, is that the longitudinal axes of the fibers are spaced radially inwardly from the inner wall of the lumen to a significant degree. Such spacing includes, for example, the thickness of the catheter sheath and any cladding on the optical fibers as well as the radial spacing between the outside periphery of the catheter and the inner lumen wall. Typically, the outermost diameter of the catheter is substantially less than the diameter of the lumen so that the catheter can pass through the lumen without difficulty. Where the laser energy is used to vaporize an obstruction in the body lumen such radial spacing of the optical fibers from the lumen wall results in drilling one or several relatively small diameter holes in the central area of the obstruction thereby leaving a substantial annular portion of the obstruction against the lumen wall.

In the case of laser angioplasty, it has been a common practice to perform a subsequent adjunctive balloon angioplasty procedure in the hope of compacting to some extent the annular portion of the obstruction that remains after the laser angioplasty procedure has been completed. Not only is the balloon angioplasty procedure a time-consuming and expensive adjunct to the laser angioplasty procedure, it adds significantly to the possibility of mechanical damage or trauma to the vessel wall and, if anything, results in a greater likelihood of restenosis than with laser angioplasty alone.

It would be desirable therefore to provide a catheter designed to enable the laser energy to impinge upon and remove or vaporize an obstruction in a body lumen as close as possible to the wall of the body lumen without thermal or mechanical damage to the lumen wall itself.

It has been suggested that inflatable balloons might be used to move the optical fibers radially inwardly and outwardly relative to the longitudinal axis of the catheter. Our aforementioned patents disclose a catheter in which an array of four optical fibers is moved along a radial plane by a balloon. U.S. Pat. Nos. 4,790,310; 5,066,292; 5,176,674; and 5,203,779 all disclose catheters which can transmit laser energy for use in laser angioplasty in which a balloon or other inflatable component is used to alter the positions of the optical fibers housed in the catheter. However, some of the prior art catheters have certain drawbacks that make their use less than optimum and in some cases potentially dangerous. For example, the aforesaid U.S. Pat. Nos. 4,790,310; 5,066,292; and 5,203,779 position the axes of the optical fibers at an outwardly diverging angle relative to the axis of the catheter. Such orientation of the optical fibers presents the danger that the laser energy will impinge upon the wall of the lumen and possibly vaporize or perforate the lumen wall. U.S. Pat. Nos. 5,176,674 and 5,203,779 teach embedding the optical fibers in the wall of the inflatable member which requires the wall to be of a greater thickness than necessary to contain the inflating fluid and therefore more difficult to inflate.

SUMMARY OF THE INVENTION

The present invention overcomes the drawbacks and disadvantages of the prior art catheter devices by providing an elastically expandable catheter containing a plurality of optical fibers arranged in an array, such as a circular array, so that each of the optical fibers is movable along a radial plane in an orientation substantially parallel to the central longitudinal axis of the catheter. The catheter of the invention is also useful in carrying out a novel method of transmitting laser energy intraluminally, and especially for use in vaporizing or removing obstructions in a body lumen, although other uses will be apparent to the skilled artisan.

Preferably, the catheter is moved to the site within the body lumen where the laser surgical procedure is to be performed by a conventional guide wire which passes through a central tube extending along a longitudinal axis of the catheter. The central tube through which the guide wire passes is flexible but need not be and is preferably not radially elastic.

A longitudinally elongate annular balloon is disposed about the central guide wire tube so as to be radially outwardly inflatable from a collapsed or deflated condition. The outermost wall of the balloon has a cylindrical shape and retains that shape as it is inflated and deflated. A plurality of optical fibers are arranged, preferably in concentric equiangular spaced relation, about the outermost periphery of the balloon and may be attached to the outermost cylindrical wall of the balloon near the distal end of the catheter. Surrounding the concentric array of optical fibers is a catheter sheath which is also elastically expandable and, preferably, has a relatively thin wall.

In this embodiment, as the balloon is inflated to expand the catheter, the spacing between the axes of adjacent fibers will increase thereby creating "dead spaces" where laser energy does not impinge upon an obstruction, for example. Such dead spaces do not pose a problem, however, since the catheter may be rotated incrementally to provide laser coverage for the dead spaces.

In an alternate embodiment of the invention, the annular space between the outermost cylindrical surface of the balloon and the innermost surface of the catheter is relatively densely packed with a plurality of optical fibers which may comprise one or more concentric rows or layers of optical fibers. The fibers are preferably not attached to the balloon nor to the catheter sheath nor to one another, but rather are permitted to shift relative to each other in the annular space between the sheath and the balloon. This arrangement provides maximum density of laser coverage at a given radius from the center of the catheter and avoids the need to rotate the catheter to obtain complete coverage.

Preferably, the free ends of the optical fibers are flush with the distal end surface of the catheter so that the ends of the fibers are in close proximity to the luminal obstruction. Inflation of the balloon moves the distal end portions of the optical fibers radially outwardly generally parallel to the longitudinal axis of the catheter so that for each inflation diameter, laser beams carried by the fibers will impinge on a different annular region. In this way, substantially full area coverage of the lumen is possible between the deflated condition and the fully inflated condition where the catheter sheath outer diameter equals the lumen diameter.

It is also contemplated within the scope of the invention that the optical fibers may be eccentrically arranged in only a limited arcuate portion of the catheter. The optical fibers are preferably quartz silica fibers suitable for transmitting most types of laser energy transmissible through an optical fiber, including continuous wave (CW), chopped and pulsed laser energy, etc., at wavelengths from about 300 nanometers up to about 2.2 microns. If desired, the proximal ends of the fibers may be scanned with a laser beam as described in our aforementioned patents with an optical or mechanical scanner or with any other suitable fiber scanning mechanism. Such scanning may be simultaneous, sequential, selective or random as is necessary for a particular application or surgical procedure. Fluid inflow and outflow to the laser surgical site is preferably achieved by the use of the central guide wire passage or by tubes extending through the central guide wire passage.

According to the method aspects of the invention, after the guide wire is inserted into the body lumen, the guide tube of the expandable catheter is threaded onto the guide wire and advanced to the surgical site, e.g., an obstruction in the lumen. When the distal end of the catheter is advanced into close proximity to or in abutment with the obstruction, the laser is energized and laser energy, e.g., pulsed laser energy, is transmitted through the optical fibers so as to impinge upon the obstruction in a first annular region located at a first radial distance from the catheter axis. Thereafter, the balloon is inflated a given amount to move the fibers radially outwardly to a greater distance so that laser energy transmitted through the fibers impinges on a second annular region located at a second radial distance from the catheter axis greater than the first radial distance. That process of inflation and laser firing is repeated with or without catheter rotation as necessary until the outermost periphery of the catheter sheath engages the inner peripheral wall of the body lumen. At that position, a thin annular rim of the obstruction substantially equal to the thickness of the catheter sheath remains disposed about the lumen wall. For safety purposes such thin rim should remain so that the laser beam does not impinge directly upon the tissue of the lumen wall.

It is a significant advantage of the present invention that a single catheter can be used in safely and effectively carrying out laser surgical procedures in body lumens of different diameters without danger of perforation or thermal damage to the lumen walls. Moreover, because the laser fibers can be positioned at different radial distances from the catheter axis by incrementally inflating the balloon, a greater area of coverage is possible with a given number of optical fibers. Because the catheter can be advanced to the surgical site in its smallest diameter deflated condition, the catheter of the invention is more readily negotiated past deviations of the body lumen from a straight line.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
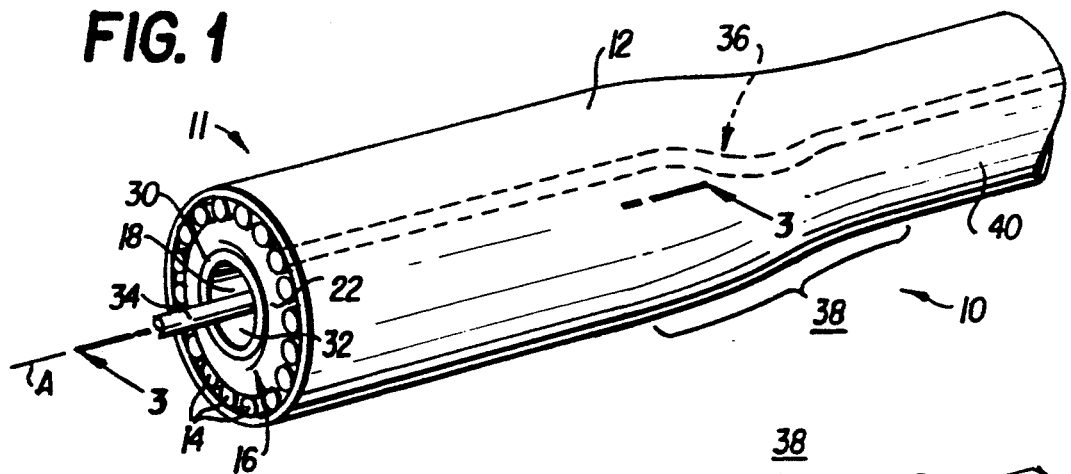
FIG. 1 is a perspective view of the distal end of the catheter of the present invention with the balloon deflated.

Referring now in detail to the drawings wherein like parts are designated by like reference numerals throughout, there is illustrated in FIG. 1 a perspective view of the distal end 11 of the catheter system of the present invention which is designated generally by reference numeral 10. Catheter system 10 generally comprises an elastically expansible catheter sheath 12 housing a plurality of optical fibers 14 arranged in a circular array about an inflatable balloon 16. Inflation and deflation of balloon 16 expands and contracts the diameters of both the optical fiber array 14 and the catheter sheath 12.

Balloon 16 is formed as an elongated cylindrical tube or toroidal element with inner and outer cylindrical walls 18, 20, respectively (FIG. 2) and annular front and rear end walls 22, 24, respectively, which define an internal cavity or space 26. Cavity 26 in the deflated condition has essentially zero volume as shown in FIG. 3 and may be inflated with a gas, such as carbon dioxide or the like, via an inflation tube 28.

The inner wall 18 of balloon 16 is supported by a flexible, but radially substantially non-elastic, central tube 30 having a bore 32 through which a guide wire 34 passes generally along the longitudinal axis A of the catheter 10. Central tube 30 has a sufficiently large diameter for the passage of fluids to and from a surgical site at the distal end 11 of the catheter 10 through bore 32 or through other tubes (not shown) disposed in bore 32. It is also contemplated that the tube 30 may have a smaller diameter sufficient to accommodate only the guide wire 34. In such case, the flow of fluids to and from the surgical site may be accomplished through the passages or interstices between the optical fibers or through separate tubes (not shown) positioned between the optical fibers.

Optical fibers 14 are arranged about the outer wall 20 of the balloon 16 preferably in equiangular spaced relation. In the embodiment shown in FIGS. 1–6, twenty (20) fibers are used for illustrative purposes only, it being understood that a greater or lesser number of fibers may be used in the annular space between the balloon 16 and sheath 12. Conventional cladded optical fibers made of quartz silica are preferably used and may have diameters in the range of about 50–200 microns. Although the overall diameter of the catheter 10 will vary depending on the particular surgical application involved, for laser angioplasty, diameters in the range of from about 1.2 to about 2.2 millimeters for the deflated condition of the balloon and from about 2.0 to about 3.0 millimeters for the fully inflated condition of the balloon are contemplated, it being understood that such ranges are not to be considered to limit the invention.

As shown in FIG. 1, in the fully deflated condition, a slight bend 36 is preferably formed in the optical fiber 14 in the transition region 38 between the distal end portion 11 housing the balloon 16 and the intermediate portion 40 of the catheter extending to the proximal end thereof (not shown). In the fully inflated condition shown in FIG. 2, the "slack" represented by bend 36 in FIG. 1 has been taken up by the elongation of the transition region 38 and the fibers 14 each have a straight inclined portion 36' in the transition region 38.

Figure 2:
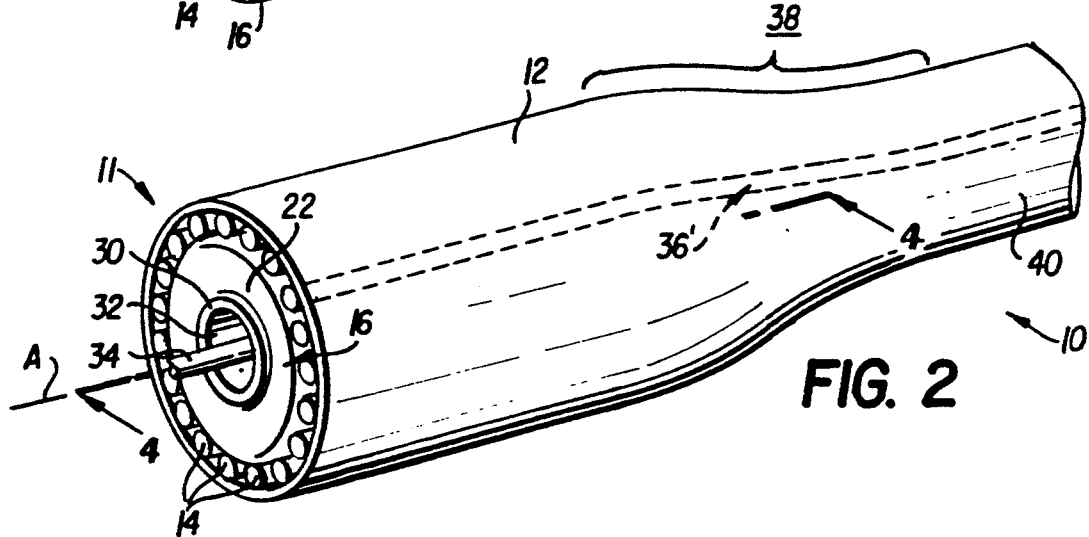
FIG. 2 is a perspective view of the distal end of the catheter of the present invention with the balloon inflated.
Figure 3:
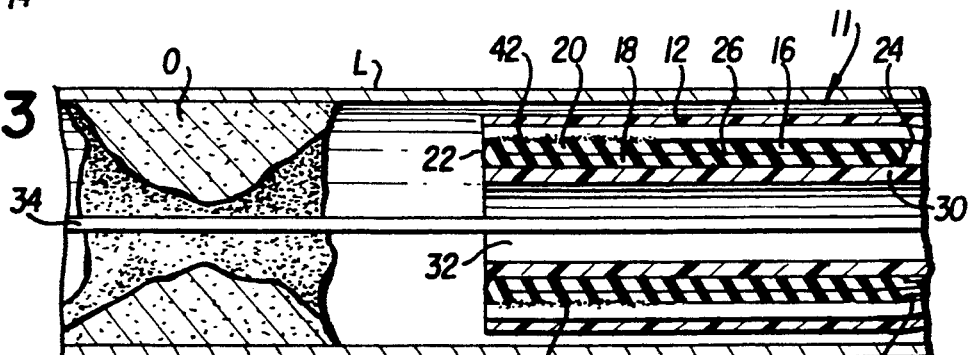
FIG. 3 is a cross-sectional view of the catheter along line 3—3 of FIG. 1 showing the catheter with the balloon deflated in a body lumen adjacent a partial occlusion of the lumen.
Figure 4:
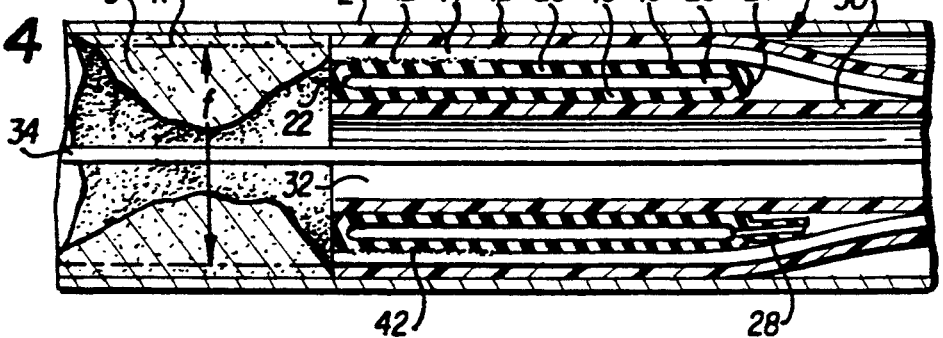
FIG. 4 is a cross-sectional view of the catheter along line 4—4 with the balloon inflated in a body lumen adjacent a partial occlusion of the lumen.

Referring to FIGS. 3 and 4 which illustrate in cross-section the catheter 10 of FIGS. 1 and 2, respectively, in the deflated and inflated conditions, the fibers 14 are shown as being attached to the outer wall 20 of the balloon by an adhesive layer 42 which is preferably a flexible adhesive, such as a silicon rubber adhesive. The adhesive layer holds each optical fiber 14 in proper orientation and does not significantly affect the elasticity of the outer wall 20 of the balloon 16.

Figure 5:
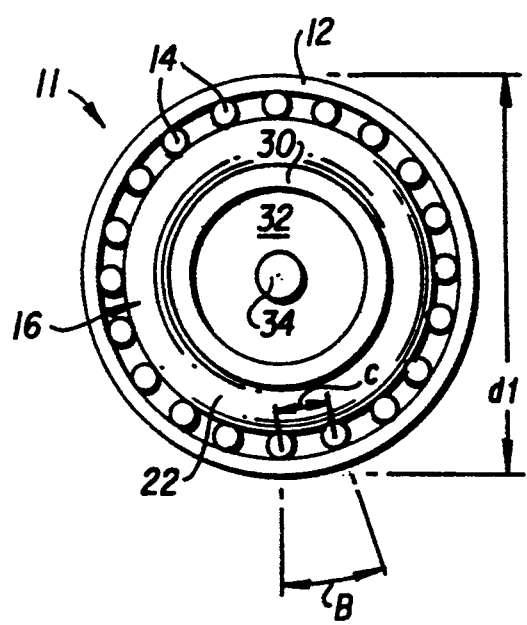
FIG. 5 is an end view of the distal end of the catheter of the present invention, with the balloon deflated.
Figure 6:
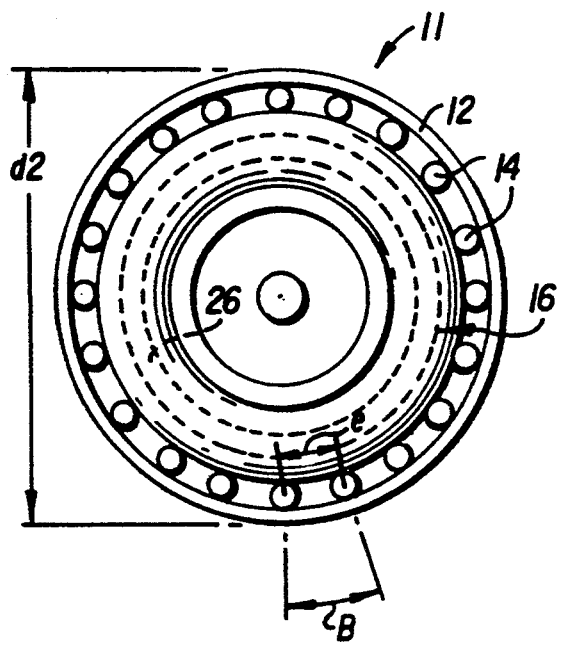
FIG. 6 is an end view of the distal end of the catheter with the balloon inflated.

FIGS. 5 and 6 illustrate end views of the distal end portion 11 of the catheter 10 of FIGS. 1 and 3 and FIGS. 2 and 4, respectively. FIG. 5 shows the catheter distal end 11 with the balloon 16 in the deflated or uninflated condition with the overall diameter of the catheter distal end 11 at a first dimension $d_1$. FIG. 6 shows the distal end 11 with the balloon in the fully inflated condition and the overall diameter of the distal end 11 at a second dimension $d_2$ greater than the first dimension $d_1$. While the angular spacing B between adjacent fibers 14 remains the same in the deflated and inflated conditions of FIGS. 5 and 6, the linear or chordal spacing c between fibers in the deflated c condition is less than the spacing e between fibers in the inflated condition. The length of the distal end 11 of the catheter is sufficient to maintain the straight and parallel orientation of the optical fibers 14 for the full range of inflation of the balloon 16. This advantageously maintains the distal ends of the fibers coplanar with the front face of the catheter so that laser energy is emitted from the ends of the fibers in an orientation parallel to the longitudinal axis A of the catheter, thus preventing undesirable impingement of laser energy on the wall of the body lumen.

Referring again to FIGS. 3 and 4, one example of use of the catheter at a surgical site will be described. As shown in FIG. 3, the guide wire 34 has been advanced in a conventional manner through a body lumen L such as a blood vessel, in which an obstruction O partially blocks the lumen. The distal end 11 of the catheter is shown with the balloon 16 in its deflated condition and the bore 32 of guide tube 30 threaded onto the guide wire 34. The catheter distal end 11 has a diameter $d_1$ (FIG. 5) less than the diameter of the lumen L so that the catheter can pass relatively easily through the lumen until the forward face of the catheter abuts the obstruction O. When that occurs, laser energy, such as pulsed laser energy, is transmitted through the optical fibers, simultaneously, sequentially or in any other appropriate manner, to vaporize or remove those portions of the obstruction confronting the fibers. The same procedure is repeated after the catheter has been rotated so that the laser beams impinge on new areas of the obstruction and is continued until the central opening in the obstruction has been enlarged to a diameter corresponding to the diameter of the optical fiber array.

Next, a gaseous fluid, such as carbon dioxide, is introduced to inflation tube 28 so as to incrementally inflate balloon 16 and move the fibers 14 radially and parallelly outwardly. Laser energy is again transmitted through the fibers to vaporize or remove additional portions of the obstruction as described above. The above steps are repeated until the distal end of the catheter is fully inflated to the position shown in FIG. 4. After treatment of the obstruction by the laser beam at the FIG. 4 position the obstruction O will be removed out to the diameter f defined by the phantom lines in FIG. 4 leaving only a thin annular rim portion R of the obstruction in the body lumen.

Gases or vapors resulting from the vaporization of the obstruction O as well as any particulate matter resulting from impingement of the laser beams on the obstruction may be carried away by suction applied to the proximal end of central tube 30 or a separate suction tube (not shown) extending through tube 30. After insertion of the catheter into abutment with the obstruction O, it may be possible to inflate the balloon to the fully inflated condition shown in FIG. 4 before operating the laser. In such case, the unvaporized material of the obstruction which is cut away from the lumen wall may be withdrawn by suction through tube 30. Advantageously, the distal end surfaces of the optical fibers directly abut the obstruction to enhance the transmission of laser energy to the obstruction.

Figure 7:
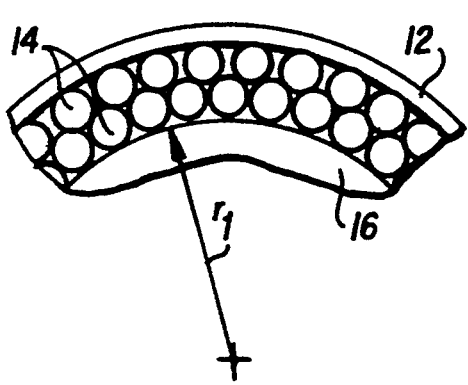
FIG. 7 is an enlarged fragmentary detail of an end view of the distal end of an alternate embodiment of the catheter of the present invention with the balloon deflated.
Figure 8:
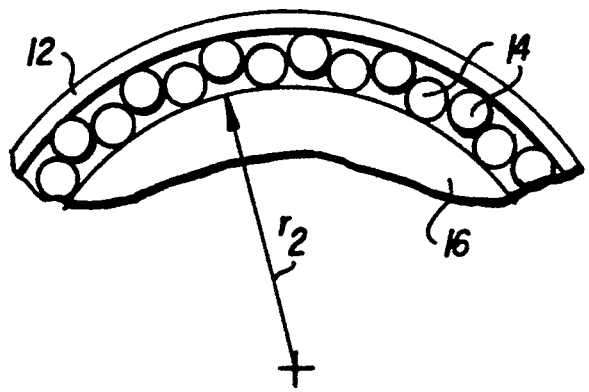
FIG. 8 is an enlarged fragmentary detail of an end view of the distal end of the FIG. 7 alternate embodiment of the catheter with the balloon inflated.

Now referring to FIGS. 7 and 8, an alternative embodiment of the invention is illustrated. In this embodiment, the annular space between the balloon 16 and catheter sheath 12 is relatively densely packed with two or more radially extending layers of optical fibers 14 comprising, for example, 100 or more fibers. In the deflated condition of the balloon 16 shown in FIG. 7, the effective radius of the optical fiber array is represented by radius $r_1$. Upon inflation of balloon 16, the optical fibers 14 tend to realign themselves relative to one another as shown in FIG. 8 with radius $r_2$ representing the new and greater effective radius of the fiber array. Continued inflation beyond the radius shown in FIG. 8 will cause the fibers to shift into a single layer of fibers with still another effective radius greater than radius $r_2$. In this embodiment, the innermost layer of fibers may be bonded to the outer surface of balloon 16 and the outermost layer of fibers may be bonded to the inner surface of catheter sheath 12. Alternately, the fibers need not be bonded to the balloon or sheath, but are permitted to assume their natural positions relative one another.

Other configurations of fiber optic arrays are contemplated within the scope of the present invention, it being understood that the invention is not intended to be limited to the two fiber optic arrays illustrated in the drawings.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What we claim is:

1. A catheter for the intraluminal transmission of laser energy comprising:
    an outer sheath having a distal end, a longitudinal axis and inner and outer surfaces;
    an inflatable balloon disposed substantially concentrically in said sheath and having a substantially cylindrical outer peripheral surface;
    a plurality of optical fibers, each having an axis and a distal end portion and being disposed in an annular space between the outer peripheral surface of said balloon and the inner surface of the sheath such that the distal end portions of said fibers are arranged substantially parallel to one another and to the longitudinal axis of the sheath;
    means for inflating said balloon from a deflated condition in which the axes of said optical fibers are located at a first radial distance from the longitudinal axis of the sheath to an inflated condition in which the axes of said optical fibers are located at a second radial distance from the longitudinal axis of the sheath greater than the first radial distance.

2. The catheter of claim 1, wherein said optical fibers are affixed to the outer peripheral surface of the balloon.

3. The catheter of claim 2, wherein said optical fibers are equiangularly spaced about the longitudinal axis of the catheter sheath.

4. The catheter of claim 1, including a central tube surrounding the longitudinal axis of the outer sheath for receiving a guide wire, said balloon having a substantially cylindrical inner peripheral surface through which said central tube extends.

5. The catheter of claim 1, wherein said optical fibers each have an end surface, the end surfaces of said optical fibers being substantially parallel to one another and oriented at substantially right angles to the longitudinal axis of the outer sheath.

6. The catheter of claim 1, wherein said optical fibers are densely packed in the annular space between the balloon and the outer sheath.

7. The catheter of claim 1, wherein said outer sheath has a substantially cylindrical shape in the inflated and deflated conditions of said balloon.

8. The catheter of claim 1, wherein said outer sheath is made of an elastically expansible material.

9. The catheter of claim 1, wherein said optical fibers comprise quartz silica fibers adapted to transmit laser energy having wavelengths in the range of from about 300 nanometers up to about 2.2 microns.

10. The catheter of claim 10, wherein said optical fibers have a diameter in the range of about 50–200 microns.

11. The catheter of claim 1, wherein said optical fibers are affixed to said balloon with a flexible adhesive.

12. The catheter of claim 1, including a tube for flowing fluid to and from the distal end of the outer sheath, said tube being disposed along the longitudinal axis of the outer sheath.

13. A catheter for the intraluminal transmission of laser energy comprising:
    a central tube having a longitudinal axis through which a guide wire is adapted to pass;
    an inflatable balloon having an elongated toroidal shape disposed about said central tube and having an exterior cylindrical surface;
    a plurality of optical fibers each having an optical axis and being affixed to the exterior cylindrical surface of said balloon such that, upon inflation of said balloon from a deflated to an inflated condition, the optical axes of said fibers are moved radially outwardly relative to the longitudinal axis of the central tube;
    an outer elastic sheath disposed concentrically about said optical fibers, said balloon and said central tube; and
    means for inflating and deflating said balloon to enlarge the diameter of said catheter and move the axes of the fibers radially outwardly.

14. The catheter of claim 13, wherein said fibers are densely packed in the space between the balloon and outer sheath.

15. The catheter of claim 13, wherein the optical fibers each have a planar end surface, the end surfaces of said fibers being arranged in substantially coplanar relation.

16. The catheter of claim 13, wherein said optical fibers comprise quartz glass fibers having a diameter of from about 50–200 microns.

17. A method of operating a catheter for intraluminal laser surgery wherein said catheter comprises an outer sheath having a distal end, a longitudinal axis and inner and outer surfaces, an inflatable balloon disposed substantially concentrically in said sheath and having a substantially cylindrical outer peripheral surface, a plurality of optical fibers, each having an axis and a distal end portion and being disposed in an annular space between the outer peripheral surface of said balloon and the inner surface of the sheath such that the distal end portions of said fibers are arranged substantially parallel to one another and to the longitudinal axis of the sheath, comprising the steps of:
    inserting the catheter with the balloon deflated into a body lumen up to an obstruction site in the lumen;

placing the distal end portions of the fibers into abutting relation with the obstruction;
transmitting laser energy through the fibers;
inflating the balloon such that the distal end portions of the fibers move radially and parallelly outwardly relative to each other and to the longitudinal axis of the sheath; and
transmitting laser energy through the fibers.

18. The method of claim 17, including the step of inserting a guide wire into the body lumen prior to inserting the catheter into the lumen and guiding the catheter to the site of the obstruction on the guide wire.

19. The method of claim 17, including the steps of:
deflating the balloon from its inflated condition;
rotating the catheter about the longitudinal axis of the sheath;
inflating the balloon such that the distal end portions of the fibers move radially and parallelly outwardly relative to each other and to the longitudinal axis of the sheath; and
transmitting laser energy through the filter.

20. The method of claim 17, wherein the optical fibers have end surfaces and including the step of placing the end surfaces of the fibers into contacting relation with the obstruction.

* * * * *